(12) United States Patent
Pan et al.

(10) Patent No.: US 11,420,911 B2
(45) Date of Patent: *Aug. 23, 2022

(54) CATALYST CONTAINING LF-TYPE B ACID AND METHOD FOR PREPARING ETHYLENE USING DIRECT CONVERSION OF SYNGAS

(71) Applicant: DALIAN INSTITUTE OF CHEMICAL PHYSICS, CHINESE ACADEMY OF SCIENCES, Dalian (CN)

(72) Inventors: Xiulian Pan, Dalian (CN); Feng Jiao, Dalian (CN); Xinhe Bao, Dalian (CN); Yuxiang Chen, Dalian (CN)

(73) Assignee: DALIAN INSTITUTE OF CHEMICAL PHYSICS, CHINESE ACADEMY OF SCIENCES, Dalian (CN)

( * ) Notice: Subject to any disclaimer, the term of this patent is extended or adjusted under 35 U.S.C. 154(b) by 70 days.

This patent is subject to a terminal disclaimer.

(21) Appl. No.: 16/963,030

(22) PCT Filed: Jan. 28, 2019

(86) PCT No.: PCT/CN2019/073389
§ 371 (c)(1),
(2) Date: Jul. 17, 2020

(87) PCT Pub. No.: WO2019/144955
PCT Pub. Date: Aug. 1, 2019

(65) Prior Publication Data
US 2020/0346993 A1 Nov. 5, 2020

(30) Foreign Application Priority Data
Jan. 26, 2018 (CN) .......................... 201810081164.X

(51) Int. Cl.
| | |
|---|---|
| *C07C 1/04* | (2006.01) |
| *B01J 23/06* | (2006.01) |
| *B01J 23/08* | (2006.01) |
| *B01J 23/10* | (2006.01) |
| *B01J 23/18* | (2006.01) |
| *B01J 23/26* | (2006.01) |
| *B01J 23/34* | (2006.01) |
| *B01J 23/745* | (2006.01) |
| *B01J 23/75* | (2006.01) |
| *B01J 29/18* | (2006.01) |
| *B01J 29/24* | (2006.01) |

(Continued)

(52) U.S. Cl.
CPC ............. *C07C 1/0425* (2013.01); *B01J 23/06* (2013.01); *B01J 23/08* (2013.01); *B01J 23/10* (2013.01); *B01J 23/18* (2013.01); *B01J 23/26* (2013.01); *B01J 23/34* (2013.01); *B01J 23/745* (2013.01); *B01J 23/75* (2013.01); *B01J 29/185* (2013.01); *B01J 29/24* (2013.01); *B01J 29/26* (2013.01); *B01J 35/1009* (2013.01); *B01J 35/1014* (2013.01); *C07C 2523/06* (2013.01); *C07C 2523/08* (2013.01); *C07C 2523/10* (2013.01); *C07C 2523/18* (2013.01); *C07C 2523/26* (2013.01); *C07C 2523/34* (2013.01); *C07C 2523/745* (2013.01); *C07C 2523/75* (2013.01); *C07C 2529/18* (2013.01); *C07C 2529/24* (2013.01); *C07C 2529/26* (2013.01)

(58) Field of Classification Search
CPC ... B01J 23/06; B01J 23/08; B01J 23/10; B01J 23/18; B01J 23/26; B01J 23/34; B01J 23/745; B01J 23/75; B01J 29/185; B01J 29/14; B01J 29/24; B01J 29/26; B01J 35/1009; B01J 2523/06; B01J 2523/08; B01J 2523/10; B01J 2523/18; B01J 2523/26; C07C 2529/26
See application file for complete search history.

(56) References Cited

U.S. PATENT DOCUMENTS

| | | | |
|---|---|---|---|
| 7,208,442 B2 | 4/2007 | Xu et al. | |
| 2010/0105548 A1* | 4/2010 | Zhang | H01M 4/925 502/313 |

FOREIGN PATENT DOCUMENTS

| | | |
|---|---|---|
| CN | 101199940 A | 6/2008 |
| CN | 103193580 A | 7/2013 |
| CN | 103331171 A | 10/2013 |

(Continued)

OTHER PUBLICATIONS

Written Opinion dated Apr. 25, 2019 for related International Patent Application No. PCT/CN2019/073389 issued by the international searching authority.

(Continued)

*Primary Examiner* — Jafar F Parsa
(74) *Attorney, Agent, or Firm* — MagStone Law, LLP; Enshan Hong

(57) ABSTRACT

A catalyst containing LF-type B acid preparing ethylene using direct conversion of syngas is a composite catalyst and formed by compounding component A and component B in a mechanical mixing mode. The active ingredient of the component A is a metal oxide; the component B is a zeolite of MOR topology; and a weight ratio of the active ingredients in the component A to the component B is 0.1-20. The reaction process has an extremely high product yield and selectivity, with the selectivity for light olefin reaching 80-90%, wherein ethylene has high space time yield and can reach selectivity of 75-80%. Meanwhile, the selectivity for a methane side product is extremely low (<15%).

16 Claims, No Drawings

(51) Int. Cl.
*B01J 29/26* (2006.01)
*B01J 35/10* (2006.01)

(56) References Cited

FOREIGN PATENT DOCUMENTS

| CN | 104888838 A | 9/2015 |
| CN | 106345514 A | 1/2017 |
| CN | 107661774 A | 2/2018 |

OTHER PUBLICATIONS

International Search Report dated Apr. 25, 2019 for related International Patent Application No. PCT/CN2019/073389 issued by the international searching authority.

\* cited by examiner

CATALYST CONTAINING LF-TYPE B ACID AND METHOD FOR PREPARING ETHYLENE USING DIRECT CONVERSION OF SYNGAS

RELATED APPLICATIONS

This is a U.S. national stage of international application No. PCT/CN2019/073389 filed on Jan. 28, 2019, which claims priority from China Patent Application No. 201810081164.X filed on Jan. 26, 2018, the entire content of which is incorporated herein as reference.

TECHNICAL FIELD

The present invention belongs to preparation of light olefin using syngas, and particularly relates to a catalyst containing LF-type B acid and a method for preparing ethylene using direct conversion of syngas.

BACKGROUND

Light olefin refers to alkene with the number of carbon atoms less than or equal to 4. Light olefin represented by ethylene and propylene are very important basic organic chemical raw materials. With the fast growth of economy in China, the market of the light olefin is in short supply for a long time. At present, the light olefin is produced mainly through a petrochemical route of cracking of light hydrocarbon (ethane, naphtha and light diesel fuel). Due to the increasing shortage of global petroleum resources and the long-term high-price operation of crude oil, the development of the light olefin industry relying only on a tubular cracking furnace technology that uses petroleum light hydrocarbon as raw material will encounter more and more difficulties in raw material. The production technology and the raw material of the light olefin must be diversified. A technology for preparing alkene using syngas can widen the source of the raw material, and will provide an alternative solution for a steam cracking technology based on high-cost raw material such as naphtha by production of syngas using crude oil, natural gas, coal and renewable material as raw material. One-step direct preparation of the light olefin using the syngas is a process of directly preparing the light olefin with the number of carbon atoms less than or equal to 4 through Fischer-Tropsch synthesis reaction of carbon monoxide and hydrogen under the action of the catalyst. This process simplifies the process flow and greatly reduces the investment unlike an indirect method that further prepares the alkene from the syngas and the methanol or dimethyl ether.

Direct preparation of the light olefin using the syngas through Fischer-Tropsch synthesis has become one of research hotspots in development of catalyst for Fischer-Tropsch synthesis. In patent CN1083415A disclosed by Dalian Institute of Chemical Physics, Chinese Academy of Sciences, high activity (CO conversion rate: 90%) and selectivity (light olefin selectivity: 66%) can be obtained under reaction pressure of 1.0 to 5.0 MPa and reaction temperature of 300 to 400° C. in preparation of the light olefin from the syngas under the auxiliary of alkali K or Cs ion by using an iron-manganese catalyst system carried by IIA alkali metal oxide such as MgO or silica rich zeolite (or phosphorous-aluminum zeolite). In patent ZL03109585.2 declared by Beijing University Of Chemical Technology, Fe/activated carbon catalyst with manganese, copper, zinc, silicon and potassium as auxiliaries is prepared by a vacuum impregnation method for the reaction of preparation of the light olefin from the syngas. Under the condition of no feedstock gas circulation, the CO conversion rate is 96%, and the selectivity of the light olefin in hydrocarbons is 68%. In 2012, professor de Jong's team at Utrecht university in Netherlands made good progress by using Fe catalyst modified by Fe, Na, S and other auxiliaries supported by SiC, carbon nanofiber and other inert carriers, obtained 61% of selectivity of light olefin. However, the selectivity is reduced when the conversion rate is increased. In the above report, the catalyst uses metal iron or iron carbide as the active ingredient. The reaction follows the chain growth reaction mechanism of metal surfaces. The selectivity of the product light olefin is low, and especially, the selectivity of a single product such as ethylene is less than 30%. In 2016, researcher Sun Yuhan and researcher Zhong Liangshu in Shanghai Advanced Research Institute reported a preferred exposure [101] and [020] manganese-assisted cobalt carbide based catalyst, and realized 60.8% of selectivity of light olefin and 5% of selectivity of methane at a CO conversion rate of 31.8%. However, the selectivity of single ethylene is less than 20%. Recently, a composite bifunctional catalyst of $ZnCr_2O_4$ oxide and hierarchical pore SAPO-34 zeolite has been reported by academician Bao Xinhe and researcher Pan Xiulian in Dalian Institute of Chemical Physics, Chinese Academy of Sciences (Jiao et al., Science 351 (2016) 1065-1068), which has realized 80% of selectivity of the light olefin when the conversion rate of CO is 17%. However, the selectivity of the ethylene is less than 30%.

SUMMARY OF THE INVENTION

The technical problem of the present invention: in the conversion process of syngas, the selectivity of ethylene is low; meanwhile, more hydrocarbons having carbon chain length greater than 3 are produced; the present invention provides a catalyst and a method for preparing ethylene using direct conversion of syngas. The invented catalyst can catalyze direct conversion of the syngas to generate light olefin. The selectivity of a single product of ethylene can reach 75-80%.

The technical solution of the present invention is: a catalyst comprises component I and component II; the component I and the component II are compounded in a mechanical mixing mode; an active ingredient of the component I is a metal oxide; and the component II is a zeolite of MOR topology.

The metal oxide is one or more than one of $MnO_x$, $Mn_aCr_{(1-a)}O_x$, $Mn_aAl_{(1-a)}O_x$, $Mn_aZr_{(1-a)}O_x$, $Mn_aIn_{(1-a)}O_x$, $ZnO_x$, $Zn_aCr_{(1-a)}O_x$, $Zn_aAl_{(1-a)}O_x$, $Zn_aGa_{(1-a)}O_x$, $Zn_aIn_{(1-a)}O_x$, $CeO_x$, $Co_aAl_{(1-a)}O_x$, $Fe_aAl_{(1-a)}O_x$, $GaO_x$, $BiO_x$, $InO_x$, $In_aAl_bMn_{(1-a-b)}O_x$ and $In_aGa_bMn_{(1-a-b)}O_x$.

The specific surface area of $MnO_x$, $ZnO_x$, $CeO_x$, $GaO_x$, $BiO_x$ and $InO_x$ is 1-100 m²/g; and a preferred specific surface area is 50-100 m²/g.

The specific surface area of $Mn_aCr_{(1-a)}O_x$, $Mn_aAl_{(1-a)}O_x$, $Mn_aZr_{(1-a)}O_x$, $Mn_aIn_{(1-a)}O_x$, $Zr_aCr_{(1-a)}O_x$, $Zn_aAl_{(1-a)}O_x$, $Zn_aGa_{(1-a)}O_x$, $Zn_aIn_{(1-a)}O_x$, $Co_aAl_{(1-a)}O_x$, $Fe_aAl_{(1-a)}O_x$, $In_aAl_bMn_{(1-a-b)}O_x$ and $In_aGa_bMn_{(1-a-b)}O_x$ is 5-150 m²/g; and a preferred specific surface area is 50-150 m²/g. A preferred specific surface area is 50-150 m²/g. The value range of x is 0.7-3.7, and the value range of a is 0-1; and the value range of a+b is 0-1.

a, b, (1−a), (1−a−b) and x in the present invention only represent the relative proportions of the chemical composition of the elements in the metal oxide. Any metal oxide with the same proportion is regarded as the same metal oxide.

The MOR zeolite in the component B contains LF-type B acid; and the content range of the LF-type B acid is 0.01 mmol/g-0.6 mmol/g, preferably 0.1-0.6 mmol/g and more preferably 0.3-0.6 mmol/g.

According to the wave number range of the infrared spectrum, the B acid of the zeolite of the MOR topology can be classified into three types: LF, HT and TF. Type LF is the B acid in an eight-membered ring pocket on the side edge of an MOR main porous channel. The fitting and attribution of the three acids are based on the literature N. Cherkasovetal./ VibrationalSpectroscopy83(2016)170-179.

The mechanical mixing in the present invention can adopt one or more than two of mechanical agitation, ball milling, rocking bed mixing and mechanical grinding for composition.

The MOR topology of the present invention is an orthorhombic crystal system, is of a one-dimensional porous channel structure with parallel elliptical straight-through porous channels and includes 8-ring and 12-ring one-dimensional straight-through porous channels. 8-ring pockets are communicated on the side edges of the 12-ring porous channels. [ATLAS OF ZEOLIE FRAMEWORK TYPES, Ch. Baerlocher et. al., 2007, Elsevier.].

As a preferred technical solution, a weight ratio of the active ingredients in the component I to the component II is 0.1-20, and preferably 0.3-8.

As a preferred technical solution, a dispersing agent is also added to the component I; the metal oxide is dispersed in the dispersing agent; and the dispersing agent is one or more than one of $Al_2O_3$, $SiO_2$, $Cr_2O_3$, $ZrO_2$, $TiO_2$, $Ga_2O_3$, activated carbon, graphene and carbon nanotube.

As a preferred technical solution, in the component I, the content of the dispersing agent is 0.05-90 wt %, and preferably 0.05-25 wt %; and the balance is an active metal oxide.

As a preferred technical solution, the skeleton element composition of the zeolite of the MOR topology may be one or more than one of Si—Al—O, Ga—Si—O, Ga—Si—Al—O, Ti—Si—O, Ti—Al—Si—O, Ca—Al—O and Ca—Si—Al—O.

The present invention also provides a method for preparing light olefin through direct conversion of syngas, which uses the syngas as reaction raw material, and conducts a conversion reaction on a fixed bed or a moving bed. The adopted catalyst is the above catalyst.

As a preferred technical solution, the pressure of the syngas is 0.5-10 MPa, and preferably 1-8 MPa; reaction temperature is 300-600° C., and preferably 300° C.-450° C.; space velocity is 300-10000 preferably 500-9000 and more preferably 500-6000 $h^{-1}$; the syngas is $H_2$/CO mixture; and the ratio of $H_2$/CO is 0.2-3.5, and preferably 0.3-2.5.

As a preferred technical solution, $C_{2-4}$ olefin is prepared using one-step direct conversion of syngas by the method; the selectivity of ethylene is 75-80%; and the selectivity of a methane side product is lower than 15%. The present invention has the following advantages:

1. Different from the traditional technology for preparing the light olefin through methanol (MTO for short), this technology realizes preparation of the light olefin through one-step direct conversion of syngas.

2. In the product, a single ethylene product has high selectivity and can reach 75-80%, and high space time yield, which is beneficial for product separation.

3. The active ingredient metal oxide of the component I in the catalyst has a higher specific surface area; therefore, the metal oxide surface has more active sites, which is more conducive to conducting a catalytic reaction.

4. On one hand, the role of the component II in the catalyst is to further convert the active gas-phase intermediate produced by the component I to obtain light olefin by coupling with the component I. The role of the component II on the balanced pull of the series reaction can promote the activation and conversion of the series reaction for the syngas and thus can increase the conversion rate. On the other hand, the special porous channel structure of the zeolite is used in the component II used in the present invention; especially, the LF-type B acid is positioned in the 8-ring pocket on the side edge of MOR, and its chemical environment and space environment are not favorable for producing molecules with more than two C atoms, thereby greatly increasing the selectivity of $C_2$ in the product; the catalyst has a unique selection effect and can obtain more ethylene products with high selectivity.

5. The functions of the present invention cannot be achieved if the component I or the component II in the present invention is used separately. For example, the selectivity of methane in the product after separate use of the component I is very high, and the conversion rate is very low. The syngas cannot be activated and converted if the component II is used separately. Only the synergistic catalysis of the component I and the component II can achieve efficient conversion of the syngas and obtain excellent selectivity. Because the component I can activate the syngas to generate a specific active gas-phase intermediate, the intermediate diffuses into the porous channel of the component II through the gas phase. The zeolite of the MOR topology selected in the present invention has special pore structure and acidity which can effectively further activate and convert the active gas-phase intermediate produced by the component I into olefin. The special porous channel structure of the component II enables the product to have special selectivity.

6. The preparation process of the composite catalyst of the present invention is simple and has mild conditions. The reaction process has an extremely high product yield and selectivity, with the selectivity for $C_2$-$C_4$ light olefins reaching 80-90%, while the selectivity for a methane side product is less than 15%. The present invention has excellent application prospect.

DETAILED DESCRIPTION OF PREFERRED EMBODIMENTS

The present invention is further illustrated below by embodiments, but the scope of claims of the present invention is not limited by the embodiments. Meanwhile, the embodiments only give some conditions for achieving the purpose, but it doesn't mean that the conditions must be satisfied to achieve the purpose.

The metal oxide in the present invention can be obtained by purchasing a commercially available metal oxide with a high specific surface area, or obtained by the following methods:

I. Preparation of Component I of Catalyst (I) ZnO material with high specific surface area was synthesized through a precipitation method:

(1) 3 parts of 0.446 g (1.5 mmol) of $Zn(NO_3)_2 \cdot 6H_2O$ were respectively weighed into three containers; 0.300 g (7.5 mmol), 0.480 g (12 mmol) and 0.720 g (18 mmol) of NaOH were respectively weighed and successively added to the above three containers; 30 ml of deionized water was weighed and added to the three containers; stirring was conducted for a time greater than 0.5 h at 70° C. to uniformly mix a solution; natural cooling was conducted to room temperature; reaction liquid was centrifugally separated to collect the centrifugally separated precipitate; and washing was conducted with deionized water twice to obtain ZnO metal oxide precursor;

(2) roasting: after drying the obtained product in the air, the product was roasted in an atmosphere to obtain ZnO material with high specific surface area. The atmosphere is inert gas, reducing gas or oxidizing gas. The inert gas is one or more than one of $N_2$, He and Ar. The reducing gas is one or two of $H_2$ and CO, and the reducing gas may also contain the inert gas. The oxidizing gas is one or more than one of $O_2$, $O_3$ and $NO_2$, and the oxidizing gas may also contain the inert gas. Roasting temperature is 300-700° C., and time is 0.5 h-12 h.

The purpose of roasting is to decompose the precipitated metal oxide precursor into oxide nanoparticles with high specific surface area at high temperature and clean the adsorbed species on the surface of the oxide generated by decomposition through the high temperature roasting treatment.

Specific samples and preparation conditions thereof are shown in Table 1 below. As a reference example, ZnO #4 in the table is a commercially available ZnO single crystal with low specific surface area.

TABLE 1

Preparation of ZnO Material and Parameter Performance

| Zinc Oxide Sample Number | Roasting Time/h | Roasting Temperature/ ° C. | Roasting Atmosphere | Specific Surface Area m²/g |
|---|---|---|---|---|
| ZnO#1 | 5 | 500 | Ar | 71 |
| ZnO#2 | 2 | 320 | 5%$H_2$/$N_2$ | 47 |
| ZnO#3 | 3 | 550 | Air | 15 |
| ZnO#4 | — | — | — | <1 |

(II) MnO Material with High Specific Surface Area was Synthesized Through a Coprecipitation Method:

The preparation process is the same as that of the above ZnO #2. The difference is that the precursor of Zn is changed for the corresponding precursor of Mn, which may be one of manganous nitrate, manganese chloride and manganese acetate, and is manganous nitrate herein. The corresponding product is defined as MnO. The specific surface area is 23 m²/g.

(III) $CeO_2$ Material with High Specific Surface Area was Synthesized Through a Coprecipitation Method:

The preparation process is the same as that of the above ZnO #2. The difference is that, the precursor of Zn is changed for the corresponding precursor of Ce, which may be one of cerium nitrate, cerium chloride and cerous acetate, and is cerium nitrate herein. The corresponding product is defined as $CeO_2$. The specific surface area is 92 m²/g.

(IV) $Ga_2O_3$ Material with High Specific Surface Area was Synthesized Through a Coprecipitation Method:

The preparation process is the same as that of the above ZnO #2. The difference is that, the precursor of Zn is changed for the corresponding precursor of Ga, which may be one of gallium nitrate, gallium chloride and gallium acetate, and is gallium nitrate herein. The corresponding product is defined as $Ga_2O_3$. The specific surface area is 55 m²/g.

(V) $Bi_2O_3$ Material with High Specific Surface Area was Synthesized Through a Coprecipitation Method:

The preparation process is the same as that of the above ZnO #2. The difference is that, the precursor of Zn is changed for the corresponding precursor of Bi, which may be one of bismuth nitrate, bismuth chloride and bismuth acetate, and is bismuth nitrate herein. The corresponding product is defined as $Bi_2O_3$. The specific surface area is 87 m²/g.

(VI) $In_2O_3$ Material with High Specific Surface Area was Synthesized Through a Coprecipitation Method:

The preparation process is the same as that of the above ZnO #2. The difference is that, the precursor of Zn is changed for the corresponding precursor of In, which may be one of indium nitrate, indium chloride and indium acetate, and is indium nitrate herein. The corresponding product is defined as $In_2O_3$. The specific surface area is 52 m²/g.

(VII) $Mn_aCr_{(1-a)}O_x$, $Mn_aAl_{(1-a)}O_x$, $Mn_aZr_{(1-a)}O_x$, $Zn_aCr_{(1-a)}O_x$, $Zn_aAl_{(1-a)}O_x$, $Zn_aGa_{(1-a)}O_x$, $Zn_aIn_{(1-a)}O_x$, $Co_aAl_{(1-a)}O_x$, $FeAl_{(1-a)}O_x$, $In_aAl_bMn_{(1-a-b)}O_x$ and $In_aGa_bMn_{(1-a-b)}O_x$ with High Specific Surface Area were Synthesized Through a Precipitation Method Zinc nitrate, aluminum nitrate, chromic nitrate, manganese nitrate, zirconium nitrate, indium nitrate, cobalt nitrate and ferric nitrate were adopted as precursors, and mixed at room temperature in water (wherein for ammonium carbonate as a precipitant, a feeding ratio is excessive or the ratio of ammonium ions to metal ions is preferably 1:1). The above mixed solution was aged, and then taken out for washing, filtering and drying; and the obtained solid was roasted under an air atmosphere to obtain a metal oxide with high specific surface area. Specific samples and preparation conditions thereof are shown in Table 2 below.

TABLE 2

Preparation of Metal Oxide with High Specific Surface Area and Performance Parameters

| Metal Oxide | Feeding Ratio of Metal Elements and Final Molar Concentration of One Metal in Water (mmol/L) | Aging Temperature ° C. | Aging Time h | Roasting Temperature ° C. | Roasting Time h | Specific Surface Area m²/g |
|---|---|---|---|---|---|---|
| $ZnCr_2O_4$ | ZnCr = 1:2, and Zn is 50 mM | 120 | 24 | 500 | 2 | 126 |
| $ZnAl_2O_4$ | ZnAl = 1:2, and Zn is 50 mM | 130 | 20 | 400 | 4 | 137 |
| $ZnGa_2O_4$ | ZnGa = 1:2, and Zn is 50 mM | 130 | 20 | 400 | 4 | 110 |
| $ZnIn_2O_4$ | ZnIn = 1:2, and Zn is 50 mM | 130 | 20 | 400 | 4 | 87 |
| $MnCr_2O_4$ | MnCr = 1:2, and Mn is 50 mM | 140 | 18 | 450 | 3 | 11 |

TABLE 2-continued

Preparation of Metal Oxide with High Specific Surface Area and Performance Parameters

| Metal Oxide | Feeding Ratio of Metal Elements and Final Molar Concentration of One Metal in Water (mmol/L) | Aging Temperature °C. | Aging Time h | Roasting Temperature °C. | Roasting Time h | Specific Surface Area m²/g |
|---|---|---|---|---|---|---|
| $MnAl_2O_4$ | MnAl = 1:2, y = 2; and Mn is 50 mM | 145 | 16 | 400 | 2 | 15 |
| $MnZr_2O_4$ | MnZr = 1:2, and Mn is 50 mM | 150 | 12 | 500 | 1 | 38 |
| $MnIn_2O_4$ | MnIn = 1:2, and Mn is 50 mM | 150 | 12 | 500 | 1 | 67 |
| $CoAl_2O_4$ | CoAl = 1:2, and Co is 50 mM | 145 | 16 | 400 | 2 | 22 |
| $FeAl_2O_4$ | FeAl = 1:2, and Fe is 50 mM | 145 | 16 | 400 | 2 | 30 |
| $InAl_3MnO_7$ | In:Al:Mn = 1:3:1, and Mn is 50 mM | 150 | 12 | 500 | 1 | 84 |
| $InGa_2MnO_7$ | In:Ga:Mn = 1:2:1; and Mn is 50 mM | 145 | 16 | 400 | 2 | 67 |

(VIII) Metal Oxide Dispersed in Dispersing Agent $Cr_2O_3$, $Al_2O_3$ or $ZrO_2$ $Cr_2O_3$, $Al_2O_3$ or $ZrO_2$ dispersed metal oxide was prepared through a precipitate deposition method by taking $Cr_2O_3$, $Al_2O_3$ or $ZrO_2$ as a carrier. By taking preparation of dispersed ZnO as an example (the specific surface area is about 5 m²/g), commercial $Cr_2O_3$, $Al_2O_3$ (the specific surface area is about 20 m²/g) or $ZrO_2$ (the specific surface area is about 10 m²/g) as a carrier was dispersed in water in advance, and then mixed and precipitated at room temperature with a sodium hydroxide precipitant by taking zinc nitrate as raw material. The molar concentration of $Zn^{2+}$ is 0.067M; and the ratio of molar fractions of $Zn^{2+}$ and the precipitant is 1:8; and then aging was conducted at 160° C. for 24 hours to obtain dispersed ZnO by taking $Cr_2O_3$, $Al_2O_3$ or $ZrO_2$ as the carrier (the contents of the dispersing agents in the component I are 0.1 wt %, 20 wt % and 85 wt %). The obtained sample was roasted at 500° C. for 1 hour in air. The products were successively defined as dispersed oxides 1-3, and the specific surface areas were successively 148 m²/g, 115 m²/g and 127 m²/g.

The same method is used to obtain dispersed MnO oxide by taking $SiO_2$ (the specific surface area is about 2 m²/g), $Ga_2O_3$ (the specific surface area is about 10 m²/g), or $TiO_2$ (the specific surface area is about 15 m²/g) as the carrier (the contents of the dispersing agents in the component I are 5 wt %, 30 wt % and 60 wt %). The products are successively defined as dispersed oxides 4-6. The specific surface areas are successively 97 m²/g, 64 m²/g and 56 m²/g.

The same method is used to obtain dispersed ZnO oxide by taking activated carbon (the specific surface area is about 1000 m²/g), graphene (the specific surface area is about 500 m²/g), or carbon nanotube (the specific surface area is about 300 m²/g) as the carrier (the contents of the dispersing agents in the component I are 5 wt %, 30 wt % and 60 wt %). The products are successively defined as dispersed oxides 7-9. The specific surface areas are successively 177 m²/g, 245 m²/g and 307 m²/g.

II. Preparation of Component II (Zeolite of MOR Topology)

The MOR topology is an orthorhombic crystal system, is of a one-dimensional porous channel structure with parallel elliptical straight-through porous channels and includes 8-ring and 12-ring one-dimensional straight-through porous channels. 8-ring pockets are communicated on the side edges of the 12-ring porous channels.

The determination of the content of the LF-type B acid may be but not limited to: firstly, a solid nuclear magnetic H spectrum or $NH_3$-TPD is used to quantitatively measure the content of all B acids in MOR; then three peaks of LF, HF and TF are fitted through vacuum in-situ infrared OH vibration peak signals; the percentage of LF in all B acids is calculated according to the relative proportion of peak area; and then the content of the LF-type B acid is calculated according to the product of the content of all B acids in MOR and the percentage of LF in all B acids. The fitting and attribution of the three acids are based on the literature N. Cherkasov et al./Vibrational Spectroscopy 83(2016)170-179.

The component II zeolite of the present invention may be a purchased commercial product (a zeolite which conforms to the content range 0.01 mmol/g-0.6 mmol/g of the LF-type B acid is selected), such as commercial mordenite from Nankai University Catalyst Plant; or commercial MOR-SAR=15 from Shentan Catalyst Company;

or a prepared zeolite, taking hydrothermal synthesis as an example herein.

1) The specific preparation process is: aluminum sulphate was mixed with a sodium hydroxide solution according to $n(SiO_2)/n(Al_2O_3)=15$, $n(Na_2O)/n(SiO_2)=0.2$, $n(H2P)/n(SiO_2)=26$; then, silica sol was added and stirred for 1 h to obtain homogeneous phase initial gel; then, the mixture was transferred into a synthesis autoclave, was statically crystallized at 180° C. for 24 h, and then was quenched, washed and dried to obtain a mordenite sample, labeled as Na-MOR.

Na-MOR was taken, mixed with 1 mol/L ammonium chloride solution, stirred at 90° C. for 3 h, washed, dried for two times in succession, and roasted at 450° C. for 6 h to obtain H-mordenite.

The skeleton element composition of the zeolite of the MOR topology prepared by the above process may be one of Si—Al—O, Ga—Si—O, Ga—Si—Al—O, Ti—Si—O, Ti—Al—Si—O, Ca—Al—O and Ca—Si—Al—O. O element of part of the skeleton is connected with H, and corresponding products are successively defined as MOR1-8.

TABLE 3

Preparation of Zeolite of MOR Topology and Performance Parameters

| Sample Number | Si and Ca Sources | Al, Ga and Ti Sources | Molar Ratio | Hydrothermal Temperature (°C.) | Time (Day) | LF Acid Amount mmol/g |
|---|---|---|---|---|---|---|
| MOR1 | TEOS | sodium metaaluminate | $n(SiO_2)/n(Al_2O_3) = 16$, $n(Na_2O)/n(SiO_2) = 0.3$ $n(H_2O)/n(SiO_2) = 27$ | 170 | 1.3 | 0.48 |
| MOR2 | silica sol Ca(OH) | Al(OH)3 | $n(SiO_2 + CaO)/n(Al_2O_3) = 8$, $n(SiO_2)/n(CaO) = 43$, $n(Na_2O)/n(SiO_2) = 0.2$ $n(H_2O)/n(SiO_2) = 26$ | 183 | 0.9 | 0.35 |
| MOR3 | TEOS | AlOOH gallium nitrate | $n(SiO_2)/n(Al_2O_3 + Ga_2O_3) = 22$, $n(Ga_2O_3)/n(Al_2O_3) = 7$, $n(Na_2O)/n(SiO_2) = 0.3$ $n(H_2O)/n(SiO_2) = 26$ | 181 | 1.3 | 0.30 |
| MOR4 | silica sol | titanium sol | $n(SiO_2)/n(TiO_2) = 70$, $n(Na_2O)/n(SiO_2) = 0.3$ $n(H_2O)/n(SiO_2) = 26$ | 188 | 0.8 | 0.25 |
| MOR5 | silica sol | aluminum sulfate | $n(SiO_2)/n(Al_2O_3) = 6$, $n(Na_2O)/n(SiO_2) = 0.2$ $n(H_2O)/n(SiO_2) = 27$ | 188 | 0.7 | 0.22 |
| MOR6 | silica sol | aluminum nitrate | $n(SiO_2)/n(Al_2O_3) = 4$, $n(Na_2O)/n(SiO_2) = 0.2$ $n(H_2O)/n(SiO_2) = 23$ | 182 | 1.1 | 0.15 |
| MOR7 | TEOS | aluminum sulfate | $n(SiO_2)/n(Al_2O_3) = 19$, $n(Na_2O)/n(SiO_2) = 0.2$ $n(H_2O)/n(SiO_2) = 28$ | 173 | 1.6 | 0.08 |
| MOR8 | silica sol | titanium sol AlOOH | $n(SiO_2)/n(Al_2O_3 + TiO_2) = 25$, $n(TiO_2)/n(Al_2O_3) = 1$, $n(Na_2O)/n(SiO_2) = 0.2$ $n(H_2O)/n(SiO_2) = 25$ | 182 | 0.9 | 0.02 |
| Commercial mordenite from Nankai University Catalyst Plant | | | | | | 0.13 |
| Commercial MOR-SAR = 15 from Shentan Catalyst Company | | | | | | 0.27 |

III. Catalyst Preparation

The component I and the component II in the required ratio were added to the container to achieve the purposes of separation, crushing, uniform mixing and the like through one or more than two of extrusion force, impact force, shear force and friction force generated by high-speed motion of the material and/or the container, so as to realize conversion of mechanical energy, thermal energy and chemical energy by regulating the temperature and the atmosphere of carrier gas, thereby further enhancing the interaction between different components.

In the mechanical mixing process, the mixing temperature can be set as 20-100° C., and the mechanical mixing process can be conducted in an atmosphere or directly in the air. The atmosphere is selected from any of the following gas:
  a) nitrogen and/or inert gas;
  b) mixed gas of hydrogen, nitrogen and/or inert gas, with the volume of hydrogen in the mixed gas being 5-50%;
  c) mixed gas of CO, nitrogen and/or inert gas, with the volume of CO in the mixed gas being 5-20%;
  d) mixed gas of 02, nitrogen and/or inert gas, with the volume of $O_2$ in the mixed gas being 5-20%, wherein the inert gas is one or more than one of helium, argon and neon.

The mechanical mixing can adopt one or more than one of mechanical agitation, ball milling, rocking bed mixing and mechanical grinding for composition. Specifically:

Mechanical stirring: mixing the component I and the component II with a stirring rod in a stirring tank; and regulating the mixing degree of the component I and the component II by controlling stirring time (5 min-120 min) and rate (30-300 r/min).

Ball milling: rolling at high speed in a grinding tank by using abrasive and the catalysts; and producing strong impact and milling on the catalysts to achieve the effects of dispersing and mixing the component I and the component II. The ratio of the abrasive (which is stainless steel, agate and quartz; and the size range is 5 mm-15 mm) to the catalysts (the mass ratio range is 20-100:1) is controlled.

Shaking table mixing: premixing the component I and the component II and placing the components into the container; realizing the mixing of the component I and the component II by controlling the reciprocating oscillation or circumferential oscillation of a shaking table; and realizing uniform mixing by regulating oscillation speed (range: 1-70 r/min) and time (range: 5 min-120 min).

Mechanical grinding: premixing the component I and the component II and placing the components into the container; and under certain pressure (range: 5 kg-20 kg), making relative motion (speed range: 30-300 r/min) by an abrader and mixed catalysts to achieve the effect of uniform mixing.

Specific catalyst preparation and parameter features are shown in Table 4.

TABLE 4

Preparation of Catalysts and Parameter Features

| Catalyst Number | Component I | Component II | Weight Ratio of I to II | Compounding Mode and Condition ||||
|---|---|---|---|---|---|---|---|
| | | | | Mechanical Agitation Rate (r/min) and Time (min) | Ball Milling Abrasive Material, Size Range and Catalyst Mass Ratio | Rocking Bed Oscillation Speed (r/min) and Time (min) | Mechanical Polishing Pressure (kg) and Relative Movement Rate (r/min) |
| A | ZnO#1 | MOR1 | 0.33 | 5, 30 | | | |
| B | ZnO#2 | MOR2 | 0.5 | 100, 250 | | | |
| C | ZnO#3 | MOR3 | 2 | | 5 mm stainless steel ball, 50:1 | | |
| D | MnO | MOR4 | 1 | | 6 mm stainless steel ball, 60:1 | | |
| E | $CeO_2$ | MOR5 | 1 | | | 5, 10 | |
| F | $Bi_2O_3$ | MOR6 | 3 | | | 60, 100 | |
| G | $In_2O_3$ | MOR7 | 3 | | | | 5, 30 |
| H | $Ga_2O_3$ | MOR8 | 1 | 100, 300 | | | |
| I | $ZnCr_2O_4$ | MOR1 | 5 | | 6 mm agate ball, 100:1 | | |
| J | $ZnAl_2O_4$ | MOR2 | 1 | | | 70, 100 | |
| K | $ZnGa_2O_4$ | MOR3 | 3 | | | | 15, 200 |
| L | $ZnIn_2O_4$ | MOR4 | 0.33 | | | | 20, 300 |
| M | $MnCr_2O_4$ | MOR5 | 1 | 100, 300 | | | |
| N | $MnAl_2O_4$ | MOR6 | 3 | | 6 mm quartz, 100:1 | | |
| O | $MnZr_2O_4$ | MOR7 | 0.33 | | 6 mm quartz, 100:1 | | |
| P | $MnIn_2O_4$ | MOR8 | 1 | | | | 10, 100 |
| Q | $CoAl_2O_4$ | MOR1 | 1 | | | 5, 10 | |
| R | $FeAl_2O_4$ | MOR2 | 3 | | | 60, 100 | |
| S | $InAl_3MnO_7$ | MOR3 | 3 | | | | 5, 30 |
| T | $InGa_2MnO_7$ | MOR4 | 1 | 100, 300 | | | |
| U | dispersed oxide 1 | MOR5 | 0.33 | | 6 mm quartz, 100:1 | | |
| V | dispersed oxide 2 | MOR6 | 1 | 100, 250 | | | |
| W | dispersed oxide 3 | MOR7 | 3 | | 5 mm stainless steel ball, 50:1 | | |
| X | dispersed oxide 4 | MOR8 | 1 | | | | 10, 100 |
| Y | dispersed oxide 5 | MOR1 | 4 | | | 50, 60 | |
| Z | dispersed oxide 6 | MOR2 | 3 | | | | 10, 100 |
| Z1 | dispersed oxide 7 | MOR3 | 20 | | 5 mm stainless steel ball, 100:1 | | |
| Z2 | dispersed oxide 8 | MORI | 16 | 100, 200 | | | |
| Z3 | dispersed oxide 9 | MORI | 0.1 | | | | 20, 100 |
| Z4 | dispersed oxide 1 | Commercial mordenite from Nankai University Catalyst Plant | 0.33 | | 6 mm quartz, 100:1 | | |
| Z5 | dispersed oxide 2 | Commercial MOR-SAR = 15 from Shentan Catalyst Company | 1 | 100, 250 | | | |

TABLE 4-continued

Preparation of Catalysts and Parameter Features

| | | | | Compounding Mode and Condition | | | |
|---|---|---|---|---|---|---|---|
| Catalyst Number | Component I | Component II | Weight Ratio of I to II | Mechanical Agitation Rate (r/min) and Time (min) | Ball Milling Abrasive Material, Size Range and Catalyst Mass Ratio | Rocking Bed Oscillation Speed (r/min) and Time (min) | Mechanical Polishing Pressure (kg) and Relative Movement Rate (r/min) |
| Reference example 1 | ZnO#4 | MOR1 | 3 | | | 20, 30 | |
| Reference example 2 | composite metal ZnCo, the molar ratio of Zn to Co is 1:1. | MOR1 | 0.33 | 5, 30 | | | |
| Reference example 3 | TiO$_2$ | MOR1 | 0.33 | 5, 30 | | | |

Example of Catalytic Reactions

A fixed bed reaction was taken as an example, but the catalyst was also applicable to a fluidized bed reactor. The apparatus was equipped with gas mass flow meters and online product analysis chromatography (the tail gas of the reactor is directly connected with the metering valve of chromatography, and thus periodic and real-time sampling and analysis will be achieved).

2 g of the above catalyst in the present invention was placed in a fixed bed reactor. The air in the reactor was replaced with Ar; and then the temperature was raised to 300° C. in the H$_2$ atmosphere, and then the syngas (H$_2$/CO molar ratio=0.2-3.5) was switched. The pressure of the syngas was 0.5-10 MPa. The temperature was raised to reaction temperature of 300-600° C., and the air velocity of the reaction raw gas was regulated to 500-10000 ml/g/h. On-line chromatography is used to detect and analyze the product.

The reaction performance can be changed by changing the temperature, pressure and space velocity. The selectivity of the light olefin (one or more than one of ethylene, propylene and butylene) in the product can reach 80-90%, and the conversion rate of the raw material is 10-60%. Because the hydrogenation activity of the surface of the metal composite of the catalysts is not high, mass production of methane is avoided. The selectivity for the methane is low, wherein the selectivity for the ethylene is 75-80%.

TABLE 5

Application and Effect of Catalysts

| Embodiment | Catalyst | GHSV (h$^{-1}$) | Temperature (° C.) | H$_2$/CO Molar Ratio | Pressure (MPa) | Ethylene Space Time Yield mmol Olefin/h · g Catalyst | Light Olefin Selectivity % | CH$_4$ Selectivity % | Ethylene Selectivity % |
|---|---|---|---|---|---|---|---|---|---|
| 1 | A | 3500 | 400 | 2 | 3.5 | 0.70 | 87 | 8 | 76 |
| 2 | B | 3000 | 400 | 1.5 | 9 | 0.52 | 87 | 7 | 78 |
| 3 | C | 1000 | 370 | 2 | 5.5 | 0.31 | 87 | 7 | 77 |
| 4 | D | 5000 | 450 | 1.5 | 3 | 0.38 | 84 | 9 | 76 |
| 5 | E | 3000 | 430 | 3 | 1.5 | 0.66 | 83 | 11 | 75 |
| 6 | F | 2000 | 380 | 0.5 | 7 | 0.68 | 84 | 13 | 75 |
| 7 | G | 3000 | 360 | 2 | 5.5 | 0.14 | 81 | 14 | 75 |
| 8 | H | 1500 | 380 | 2.5 | 5 | 0.10 | 80 | 14 | 75 |
| 9 | I | 2300 | 350 | 1 | 3 | 1.16 | 88 | 6 | 78 |
| 10 | J | 3000 | 410 | 2.5 | 8 | 0.91 | 90 | 5 | 80 |
| 11 | K | 5000 | 400 | 2 | 4 | 0.86 | 90 | 5 | 80 |
| 12 | L | 2500 | 120 | 1 | 2 | 0.56 | 86 | 7 | 75 |
| 13 | M | 8000 | 470 | 0.5 | 1 | 0.28 | 80 | 9 | 75 |
| 14 | N | 4000 | 410 | 3 | 3 | 0.12 | 81 | 10 | 75 |
| 15 | O | 5000 | 370 | 2 | 4 | 0.22 | 83 | 14 | 75 |
| 16 | P | 3000 | 370 | 1.5 | 6.8 | 0.21 | 83 | 15 | 75 |
| 17 | Q | 3500 | 350 | 1 | 5 | 0.46 | 85 | 9 | 78 |
| 18 | R | 3000 | 450 | 0.5 | 5.8 | 0.53 | 83 | 8 | 77 |
| 19 | S | 2000 | 430 | 1 | 7 | 0.82 | 89 | 7 | 80 |
| 20 | T | 7000 | 410 | 2.5 | 2 | 0.54 | 83 | 8 | 76 |
| 21 | U | 2500 | 370 | 1.5 | 7 | 0.62 | 84 | 8 | 77 |
| 22 | V | 3000 | 350 | 2 | 5 | 0.48 | 82 | 11 | 75 |
| 23 | W | 2000 | 350 | 1 | 4 | 0.22 | 83 | 13 | 75 |

TABLE 5-continued

Application and Effect of Catalysts

| Embodiment | Catalyst | GHSV (h$^{-1}$) | Temperature (° C.) | H$_2$/CO Molar Ratio | Pressure (MPa) | Ethylene Space Time Yield mmol Olefin/h · g Catalyst | Light Olefin Selectivity % | CH$_4$ Selectivity % | Ethylene Selectivity % |
|---|---|---|---|---|---|---|---|---|---|
| 24 | X | 2500 | 410 | 1.5 | 6 | 0.06 | 81 | 15 | 75 |
| 25 | Y | 4000 | 400 | 2 | 4 | 0.80 | 89 | 9 | 77 |
| 26 | Z | 3500 | 410 | 3.5 | 3 | 0.76 | 88 | 8 | 77 |
| 27 | Z1 | 8000 | 450 | 1.5 | 1 | 0.22 | 80 | 14 | 75 |
| 28 | Z2 | 4000 | 410 | 3 | 3.5 | 0.21 | 81 | 12 | 75 |
| 29 | Z3 | 2500 | 400 | 0.5 | 10 | 0.10 | 81 | 7 | 75 |
| 30 | Z4 | 4000 | 360 | 1 | 4 | 0.23 | 80 | 14 | 75 |
| 31 | Z5 | 5000 | 375 | 1 | 3 | 0.35 | 80 | 13 | 75 |
| 32 | Reference example 1 | 1000 | 300 | 0.5 | 1 | 0.01 | 35 | 55 | 20 |
| 33 | Reference example 2 | 4000 | 450 | 3 | 3 | 0.66 | 33 | 35 | 11 |
| 34 | Reference example 3 | 2000 | 350 | 2.5 | 3 | 0.01 | 25 | 70 | 11 |
| 35 | Reference example 4 | 3000 | 400 | 1 | 4 | 0.08 | 55 | 7 | 19 |
| 36 | Reference example 5 | 3000 | 400 | 2 | 3.5 | 0.03 | 34 | 11 | 11 |
| 37 | Reference example 6 | 2500 | 400 | 2 | 3.5 | 0.05 | 45 | 19 | 30 |
| 38 | Reference example 7 | 2500 | 400 | 2 | 3.5 | 0.02 | 25 | 23 | 7 |
| 39 | Reference example 8 | 3000 | 450 | 2.5 | 4 | <0.01 | 1.5 | 50 | 0.8 |
| 40 | Reference example 9 | 2200 | 450 | 3 | 2 | <0.01 | — | — | — |
| 41 | Reference example 10 | 3000 | 420 | 3 | 2 | <0.2 | 37 | 38 | 14 |

The catalyst adopted in reference example 4 replaces the zeolite of the catalyst A with the commercial SAPO-34 purchased from Nankai University Catalyst Factory.

The catalyst adopted in reference example 5 replaces the zeolite of the catalyst A with commercial ZSM-5 of full micropore structure with Si/Al=30, purchased from Nankai University Catalyst Factory.

Reaction results of reference examples 4 and 5 show that, the MOR topology is crucial to the selective modulation of the products; SAPO$_3$4 has an orifice size of 3.8 A, and is suitable for C2-C4 hydrocarbons, but more C3 products are produced and the selectivity for ethylene is not high. The ZSM5 has larger orifice size of 5.6 A, and the products are mainly C4 hydrocarbons and even hydrocarbons with longer carbon chains.

The MOR has large orifice size of 6.5×7.0 A, but also contains a side pocket of 8-ring orifice. The depth of the pocket is shallower than that of the SAPO34 pocket. Thus, ethylene with two carbon atoms is mainly produced, and has advantageous features not found in other structural zeolites. The acid at the LF site is mainly located in the 8-ring pocket, and thus is crucial for the production of the ethylene.

The catalyst used in reference example 6 is basically consistent with the catalyst C sample, and the differences are that the sodium nitrate is used for ion exchange of the MOR3 zeolite; the LF-type B acid is partially replaced with Na; the content of the LF acid is measured as 0.005 mmol/g through solid nuclear magnetic resonance hydrogen spectroscopy and infrared quantitative measurement, while the retained contents of HF and TF acids are 0.6 mmol/g and 0.3 mmol/g respectively.

The determination of the content of the LF-type B acid may be but not limited to: firstly, a solid nuclear magnetic H spectrum or NH$_3$-TPD is used to quantitatively measure the content of all B acids in MOR; then three peaks of LF, HF and TF are fitted through vacuum in-situ infrared OH vibration peak signals; the percentage of LF in all B acids is calculated according to the relative proportion of peak area; and then the content of the LF-type B acid is calculated according to the product of the content of all B acids in MOR and the percentage of LF in all B acids. The fitting and attribution of the three acids are based on the literature N. Cherkasov et al./Vibrational Spectroscopy 83(2016)170-179.

The catalyst used in reference example 7 is basically consistent with the catalyst C sample, and the differences are that the sodium nitrate is used for ion exchange of the MOR3 zeolite; the LF-type B acid is replaced with Na; the content of the LF acid is measured as 0.001 mmol/g through solid nuclear magnetic resonance hydrogen spectroscopy and infrared quantitative measurement, while the retained contents of HF and TF acids are 0.5 mmol/g and 0.3 mmol/g respectively. The reaction results show that the LF acid in MOR is critical to the space time yield of the ethylene. When the acid of LF is lower than the scope of the claims, the ethylene yield drops sharply. After the acid of LF is almost completely replaced, the ethylene yield also correspondingly drops to be extremely low, indicating the importance of the LF acid for the direct preparation of the ethylene by using syngas.

The catalyst adopted in reference example 8 is a sample containing only component I ZnO #1 without the component II, and the reaction conversion rate is very low. The products mainly comprise by-products such as dimethyl ether and methane, and almost no ethylene is produced.

The catalyst adopted in reference example 9 is a sample containing only the zeolite of component II without the component I, and the catalytic reaction almost has no activity.

Reference examples 8 and 9 indicate that reaction effects are extremely poor when only component I or component II exists, and do not have the excellent reaction performance in the present invention.

Embodiments Z4 and Z5 are commercially available zeolites. Because the acid content meets the requirements of the present invention, the zeolites exhibit excellent catalytic performance.

The catalyst adopted in reference example 10 replaces the zeolite of the catalyst A with the commercial MOR-SAR=5 purchased from Shentan Catalyst Company. Because the acid amount of LF in the zeolite is less than 0.01 mmol/g and a gas-phase intermediate generated on the metal oxide cannot be converted well, a large amount of methane is produced and the requirements of the present invention cannot be satisfied. Therefore, it is very important to select a proper commercial zeolite.

It is observed from the above table that, the structure of the zeolite including the MOR topology, and the matching between the metal oxide and the zeolite are crucial and directly affect the selectivity of the light olefin and the ethylene.

The invention claimed is:

1. A catalyst, comprising a component I and a component II, which are compounded in a mechanical mixing mode; wherein, an active ingredient of the component I is a metal oxide; the component II is a zeolite of MOR topology;

the metal oxide is at least one of $MnO_x$, $Mn_aCr_{(1-a)}O_x$, $Mn_aAl_{(1-a)}O_x$, $Mn_aZr_{(1-a)}O_x$, $Mn_aIn_{(1-a)}O_x$, $ZnO_x$, $Zn_aCr_{(1-a)}O_x$, $Zn_aAl_{(1-a)}O_x$, $Zn_aGa_{(1-a)}O_x$, $CeO_x$, $CO_aAl_{(1-a)}O_x$, $Fe_aAl_{(1-a)}O_x$, $GaO_x$, $BiO_x$, $InO_x$, $In_aAl_bMn_{(1-a-b)}O_x$, and $In_aGa_bMn_{(1-a-b)}O_x$, a specific surface area of $MnO_x$, $ZnO_x$, $CeO_x$, $GaO_x$, $BiO_x$ and $InO_x$ is 1-100 m$^2$/g;

a specific surface area of $Mn_aCr_{(1-a)}O_x$, $Mn_aAl_{(1-a)}O_x$, $Mn_aZr_{(1-a)}O_x$, $Mn_aIn_{(1-a)}O_x$, $Zn_aCr_{(1-a)}O_x$, $Zn_aAl_{(1-a)}O_x$, $Zn_aGa_{(1-a)}O_x$, $Zn_aIn_{(1-a)}O_x$, $Co_aAl_{(1-a)}O_x$, $Fe_aAl_{(1-a)}O_x$, $In_aAl_bMn_{(1-a-b)}O_x$, and $In_aGa_bMn_{(1-a-b)}O_x$ is 5-150 m$^2$/g;

a value range of x is 0.7-3.7, and a value range of a is 0-1; and a value range of a+b is 0-1;

the MOR zeolite in the component B comprises LF-type B acid; and the content range of the LF-type B acid is 0.01 mmol/g-0.6 mmol/g, wherein the MOR has a topology being an orthorhombic crystal system, being of a one-dimensional porous channel structure with parallel elliptical straight-through porous channels, and comprising 8-ring and 12-ring one-dimensional straight-through porous channels, with the 8-ring one-dimensional straight-through porous channel communicating on side edges of the 12-ring porous channel, the 8-ring porous channel has a pocket structure, and the LF-type B acid is present in the pocket structure of the 8-ring porous channel.

2. The catalyst according to claim 1, wherein a weight ratio of the active ingredients in the component I to the component II is 0.1-20.

3. The catalyst according to claim 1, wherein a dispersing agent is also added to the component I; the metal oxide is dispersed in the dispersing agent; and the dispersing agent is at least one of $Al_2O_3$, $SiO_2$, $Cr_2O_3$, $ZrO_2$, $TiO_2$, $Ga_2O_3$, activated carbon, graphene, and carbon nanotube.

4. The catalyst according to claim 1, wherein, in the component I, the content of the dispersing agent is 0.05-90 wt %, and the balance is the metal oxide.

5. The catalyst according to claim 1, wherein a skeleton element composition of the zeolite of the MOR topology is at least one of Si—Al—O, Ga—Si—O, Ti—Si—O, Ti—Al—Si—O, Ca—Al—O, and Ca—Si—Al—O.

6. A method for preparing light olefin comprising converting syngas to the light olefin in the presence of the catalyst of claim 1.

7. The method according to claim 6, wherein the converting is carried out under a pressure of 0.5-10 MPa, a reaction temperature of 300-600° C., a space velocity of 300-10000 h$^{-1}$, and the syngas is a $H_2$/CO mixture with a ratio of $H_2$/CO of 0.2-3.5.

8. The method according to claim 6, wherein the light olefin comprises $C_{2-4}$ olefin, and the method achieves a selectivity for ethylene of 75-80%, and a selectivity for a methane side product of lower than 15%.

9. The catalyst according to claim 1, wherein the specific surface area of $MnO_x$, $ZnO_x$, $CeO_x$, $GaO_x$, $BiO_x$ and $InO_x$ is 50-100 m$^2$/g, the specific surface area of $Mn_aCr_{(1-a)}O_x$, $Mn_aAl_{(1-a)}O_x$, $Mn_aZr_{(1-a)}O_x$, $Mn_aIn_{(1-a)}O_x$, $Zn_aCr_{(1-a)}O_x$, $Zn_aAl_{(1-a)}O_x$, $Zn_aGa_{(1-a)}O_x$, $Zn_aIn_{(1-a)}O_x$, $CO_aAl_{(1-a)}O_x$, $Fe_aAl_{(1-a)}O_x$, $In_aAl_bMn_{(1-a-b)}O_x$, and $In_aGa_bMn_{(1-a-b)}O_x$ is 50-150 m$^2$/g.

10. The catalyst according to claim 2 wherein the weight ratio of the active ingredients in the component I to the component II is 0.3-8.

11. The catalyst according to claim 4, wherein in the component I, the content of the dispersing agent is 0.05-25 wt %.

12. The method according to claim 7, wherein the pressure is 0.5-10 MPa, the reaction temperature is 300° C.-450° C., the space velocity is 500-9000 h$^1$, and the ratio of $H_2$/CO is 0.3-2.5.

13. The method according to claim 12, wherein the pressure is 1-8 MPa; and the space velocity is 500-6000 h$^{-1}$.

14. The catalyst according to claim 1, wherein the content range of the LF-type B acid is 0.1-0.6 mmol/g.

15. The catalyst according to claim 1, wherein the content range of the LF-type B acid is 0.3-0.6 mmol/g.

16. The catalyst according to claim 1 wherein the metal oxide consists of at least one of $MnO_x$, $Mn_aCr_{(1-a)}O_x$, $Mn_aAl_{(1-a)}O_x$, $Mn_aIn_{(1-a)}O_x$, $ZnO_x$, $Zn_aCr_{(1-a)}O_x$, $Zn_aAl_{(1-a)}O_x$, $Zn_aGa_{(1-a)}O_x$, $Zn_aIn_{(1-a)}O_x$, $CeO_x$, $Co_aAl_{(1-a)}O_x$, $Fe_aAl_{(1-a)}O_x$, $GaO_x$, $BiO_x$, $InO_x$, $In_aAl_bMn_{(1-a-b)}O_x$, and $In_aGa_bMn_{(1-a-b)}O_x$.

* * * * *